United States Patent [19]

Abe

[11] 4,350,625

[45] Sep. 21, 1982

[54] SUBSTANCE WITH FIBRINOLYTIC ACTIVITY AND METHOD OF MANUFACTURING THE SAME

[76] Inventor: Takeshi Abe, 36-5, Kitazawa 1-chome, Setagaya-ku, Tokyo, 115, Japan

[21] Appl. No.: 201,390

[22] PCT Filed: Nov. 16, 1979

[86] PCT No.: PCT/JP79/00296
§ 371 Date: Jul. 20, 1980
§ 102(e) Date: Jul. 3, 1980

[87] PCT Pub. No.: WO80/01039
PCT Pub. Date: May 29, 1980

[30] Foreign Application Priority Data

Nov. 20, 1978 [JP] Japan .............................. 53-143224

[51] Int. Cl.$^3$ .................. A23J 1/00; C09H 1/00; A61K 37/00
[52] U.S. Cl. ................. 260/112 R; 424/98; 424/177
[58] Field of Search ............. 424/98, 177; 260/112 R

[56] References Cited

U.S. PATENT DOCUMENTS 3,711,376 1/1973 Hatton .................................. 424/98
3,819,605 6/1974 Holleman .............................. 424/98

OTHER PUBLICATIONS

Hawley-Condensed Chemical Dictionary 9th edit., pp. 769, 950.
Morrison et al.-Organic Chemistry, (2nd edit.), pp. 1100 and 1101.
Dorlands Medical Dictionary-25th edit., pp. 586, 1206 and 1606.
Astrup et al.-Arch. Biochem. Biophys., vol. 40 (1952), pp. 346-351.
Ouyang et al.-Chem. Abst., vol. 83, (1975), p. 1925f.
Heftmann-Chromatography (3rd edit.), (1975), pp. 55-69.
Britannica World Language Dictionary, p. 566.
Chrispeels-Molecular Techniques and Approaches in Dev. Biology (1973), pp. 362-383.
Ouyang et al.-Chem. Abst., vol. 89, (1978), p. 86056v, vol. 84, (1976), p. 117,481h, vol. 92, (1980), p. 53958z.
Ouyang et al.-Biochim. et Biophys. Aeta, vol. 420, 1976, pp. 298-308.

Primary Examiner—Sam Rosen
Attorney, Agent, or Firm—McGlew and Tuttle

[57] ABSTRACT

This invention relates to a new fibrinolytic substance and the method of manufacturing the same which can be singly isolated from venom of venomous snakes belonging to the family of Trimeresurus taxonomically by means of molecular sieve chromatography and ion exchange chromatography. This substance has the action of dissolving fibrin in mammals by activating plasminogen and its clinical use a fibrinolytic agent is promising.

7 Claims, 3 Drawing Figures

SUBSTANCE WITH FIBRINOLYTIC ACTIVITY AND METHOD OF MANUFACTURING THE SAME

DESCRIPTION

1. Technical Field

This invention relates to a new substance which is obtained from venom of venomous snakes belonging to the family of trimeresurus taxonomically and which has fibrinolytic activity to mammals, and a method of manufacturing the same and its applications in medicine.

2. Background Art

In general, animal toxin such as venom of snakes is known to involve various proteinic toxin factors, some of which may endorse the presence of materials showing various biochemical actions such as, for example, hemorrhagic toxin, neurotoxin, hemolytic constituent, hemopexis constituent, etc. Recent years have witnessed biochemical studies of these animal toxins which are well in progress.

Taking note of the action of the venom of Trimeresurus which is feared to have very often caused fatalities to human life and cattle, the present inventor has long been engaged in studying the action of protein toxin, and their effects on the blood coagulation system, fibrinolytic system and plastocyte function. He has discovered that a substance obtained by a special treatment of crude venom of Trimeresurus has a strong fibrinolytic activity and, as the result of further investigation, he has succeeded in isolating such substance singly and moreover, found that it has an extensive range of clinical uses as a fibrinolytic agent.

DISCLOSURE OF INVENTION

The principal object of the present invention resides in providing a new singly isolated substance, a method of manufacturing the same and its applications in medicine, said new substance being obtained by fractionating a solution of crude venom of Trimeresurus by means of so-called molecular sieve chromatography as the main procedure using a stationary phase of material having a molecular sieve effect, in combination with ion exchange chromatography using a stationary phase of ion exchange material so as to collect fractions of the largest activity of fibrinolysis each time in the aforesaid chromatographic procedure. The present invention will be explained in detail centering on preferred embodiments hereinafter.

Crude venom of Trimeresurus for use as the material in the present invention is defined and is to be understood as toxin which can be obtained from venomous snakes belonging to the family of Trimeresurus Crotalidae by classification, for example, *Trimeresurus flavoviridis, Trimeresurus tokarensis, Trimeresurus okinavensis, Trimeresurus mucrosquamatus, Trimeresurus elegans, Trimeresurus stejnegsi, Trimeresurus tinkami, Trimeresurus moticola,* and *Trimeresurus gracilis.*

A freezedried powder of crude venom obtained from one or more of these venomous snakes, is dissolved in a suitable solvent, for example, distilled water, physiological saline or a buffer solution of pH within the range of 6 to 8. This solution is fractionated by the so-called molecular sieve chromatography using a stationary phase of material having a molecular sieve effect. For example, a suitable gel filtration agent such as Sephadex (G-75 or G-100) (Trade name) or Biogel (Trade name) is used as a column filler in which said solution is adsorbed and permeated and subsequently, the resulting solution thus adsorbed and permeated is eluted in a buffer solution of suitable electrolyte of pH, about 6–8, thereby enabling it to be fractionated into 4 fractions, P-I, P-II, P-III and P-IV. Each of these fractions is tested by the standard fibrin plate method so that the fraction P-II can be ensured to have an activity of fibrinolysis.

This fraction, P-II is subjected to dialysis in distilled water and the internal solution after dialysis is freezedried. Subsequently, the fraction P-II thus freezedried is dissolved in a buffer solution of pH around 6 such as sodium acetate buffer solution and the resulting solution is fractionated by ion exchange chromatography. Namely, it is adsorbed in a column filled with CM cellulose as a cation exchange body at low temperature and the portion thus adsorbed is eluted in a buffer solution by slowing increasing salt concentration in the buffer solution so that a portion having the largest activity of fibrinolysis can be collected, and freezedried. Since this fraction is found to contain one or more kinds of impurities by SDS electrophoresis, it is further subjected to a refining step by molecular sieve chromatography. Specifically the fraction obtained by ion exchange chromatography which is then freezedried, is dissolved in a buffer solution of pH within the range of 6–8 and the resulting solution is adsorbed in a column filled with Sephadex (G-50) and the portion thus adsorbed is eluted in a similar buffer solution so that a substance having an activity of fibrinolysis can be isolated as the objective of the present invention. This substance is found to be a single chemical compound by SDS electrophoresis.

Sephadex G-50 is a kind of cross-linked dextran permitting protein of a molecular weight, less than 10,000, to be diffused in its gel particles, having a cross-linking extent of water regain, 5 g/g (dry particles) and Sephadex G-75 is capable of fractionating protein of a molecular weight, less than 40,000, and having a cross-linking extent, water regain 7.5 g/g.

Although Sephadex and Biogel have been exemplified as gel filtration agents of polysaccharide hereinbefore, other gel filtration agents having such molecular sieve effect can also be used in a like manner. At the same time, the ion exchange material is not restricted to CM cellulose but it is also possible to select some other suitable material which is compatible with the pH of the effluent in use. The preferred buffer solutions can be enumerated such as sodium citrate buffer solution, acetic acid buffer solution, phosphoric acid buffer solution and boric acid buffer solution.

The above mentioned operations are possible at ordinary temperature (room temperature) but lower temperature is better, for example, 5° C. is found most suitable.

Although the above mentioned operations of crude venom have been carried out in the order of molecular sieve chromatography using Sephadex (G-100), subsequently, ion exchange chromatography and molecular sieve chromatography using Sephadex (G-50) as a further refining step, such order is only one example. In other words, ion exchange chromatography may be carried out first or last as a refining step so that the same purpose may be achieved.

The substance with fibrinolytic activity thus obtained may be dissolved, as is, in physiological saline to produce an injection. It may also be treated by the conventional procedure for making it suitable for use as a medicine according to necessity.

The physical properties of the fibrinolytic substance of the present invention are that it is soluble in water, its sugar content can be recognized by the Anthrone method and it is a glycoprotein having its maximal absorption spectrum at 620–640 nm.

According to gel filtration with Sephadex (G-50) and disc electrophoresis, its molecular weight is presumed to be 28,000–32,000 and its total nitrogen content is 12.4±1%. This substance shows its absorption spectrum with ultraviolet ray at the maximal wavelength 278 nm. An infrared absorption spectrum of this substance by the KBr tablet method is shown in FIG. 3 and its maximal absorption of large scale is located in the neighbourhood of wavenumber, 3400, 1435, and 1350 and its maximal absorption of medium scale in the neighbourhood of wavenumber, 1640, 1100 and 925 and its maximal absorption of small scale in the neighbourhood of wavenumber, 780 respectively.

The composition of amino acids of this substance by an amino-acid analyser is shown in Table 1 and FIG. 4.

TABLE 1

| Amino acid | N mol |
| --- | --- |
| Aspartic acid | 15.366 |
| Threonine | 7.132 |
| Serine | 5.578 |
| Glutamic acid | 9.797 |
| Glycine | 9.475 |
| Alanine | 7.668 |
| Cystine | 5.454 |
| Valine | 7.422 |
| Methionine | 2.936 |
| Isoleucine | 4.836 |
| Leucine | 7.215 |
| Tyrosine | 8.923 |
| Phenylalanine | 2.895 |
| Lysine | 17.729 |
| Ammonia | 13.278 |
| Histidine | 1.793 |
| Arginine | 3.674 |

Tests of pharmacological effect of this substance were made by fibrinolysis of fibrin plate and by Chandler Loop test (Chandler, A. B. Lab. Invest., 7, 110 (1958): Conner, W. E. & Poole, J. C. F. Quart. J. Exp. Physiol. 40 1 (1961).). The first mentioned method has a measuring principle which consists in measuring the dissolved area of a fibrin plate as a substrate due to the fibrinolytic activity of the test material thus enabling the activity to be observed. The second method consists in measuring the ability of the substance for dissolving artificial thrombus formed in a loop tube.

The fibrin plate for use in the present invention is one which does not contain plasminogen (precursor of plasmin).

First of all, in the case of causing the substance of the present invention only to act on the fibrin plate, no dissolving effect can be seen and therefore, the substance has no plasmin action. On the other hand, in the case of causing a mixed solution of purified plasminogen and the present substance to act on the fibrin plate, there is noted an outstanding fibrinolytic action as compared with a control solution containing plasminogen only. (See FIG. 2). For the sake of confirmation, when the present substance is allowed to act on the standard fibrin plate, its apparently dissolving tendency can be recognized and therefore, the mode of action can be determined as an activator like action.

Also by the Chandler Loop method, the present substance showed a marked effect of dissolving thrombus.

As shown in the above mentioned pharmacological test results, the new substance having such fibrinolytic activity as is disclosed in the present application is expected to develop the undermentioned clinical effects due to the fact that it can activate plasminogen to become plasmin capable of dissolving fibrin.

In general, fibrin converted from fibrinogen by an enzymatic action is known to be one of the serious causes of thrombosis and embolism.

Owing to the aforesaid action of this substance, the inventive substance is expected to develop a prophylactic and therapeutic effect on peripheral arteriovenous thrombosis, pulmonary embolism, coronary infarction, myocardinal infarction, cerebral blood vessel infarction, thrombosis of retinal artery and vein, hemorrhage of the vitreous body, hyphema and other such diseases. Moreover, in combination with a carcinostatic agent, the present substance is expected to show synergistic action for the therapy of cancer. In addition, the present substance may be useful as anticoagulants in blood transfusion and an agent for preventing embolus formation at a suture line in vasotomy or for prolonging the physical functions of arteriovenous shunt in blood dialysis.

In the case of using the present substance in therapy, it may be administered by intravenous injection or local irrigation as the case may be.

While its doses are different depending on the kind of disease and its administration, and also, age, body weight of patients and seriousness of symptoms, a sufficient therapeutic effect can be obtained with a single dose of 0.1–80 mg for adults in most cases. Experimental examples of its pharmacology are shown as follows.

EXPERIMENT 1

Acute toxicity of the present substance was tested in groups of male mice of ddN (body weight 21±2 g), each group consisting of 10 mice, by intravenous injection to show $LD_{50}$, 20 mg/kg after 72 hours, by calculation of Litchfield & Wilcoxon's method.

EXPERIMENT 2

For the purpose of determining the fibrinolytic action of the present substance, when a sample of protein concentration, 450 μg/ml is applied to a fibrin plate (plasminogen free fibrin plate manufactured by Kowa Co., Ltd., ditto hereinafter), it does not dissolve the fibrin plate. Therefore, the present substance has no plasmin activity.

EXPERIMENT 3

A physiological salt solution of purified plasminogen (manufactured by KABI Company), 5 cu/ml was prepared. 50 μl of this solution was mixed with 100 μl of each of solutions consisting of the present substance dissolved in a Tris-HCl 0.05 M buffer solution (pH 7.4) to produce said solutions of protein concentration, 40, 120, 370, 950 and 1900 μg/ml respectively. Then 5 μl of the resulting mixed solution was poured onto a hole formed on a fibrin plate to cause its action thereon.

After leaving it alone at 37° C. for 20 hours, the dissolved area of the fibrin plate was measured, thus determining an activator action of the present substance. The fibrin plate used in this experiment is noted to show a dissolved ring with a clear border corresponding to the fibrinolytic action of the substance. The diameter of this ring is rectilinear proportion to a logarithm of fibrinolytic activity (concentration) so that the activity as an activator can be observed by measuring such diameter. The results of this measurement are shown in Table 2 and FIG. 2.

In Table 2, the activity of this substance as an activator prove to be an outstanding one as compared with a control (plasminogen only) and this activity as an activator turns out to be dose-dependent.

TABLE 2

| Protein concentration | Frequency of test | | | | |
|---|---|---|---|---|---|
| | 1 | 2 | 3 | 4 | Average |
| 40 (μg/ml) | 5.60 | 5.45 | 5.40 | 5.55 | 5.50 |
| 120 | 6.40 | 6.15 | 6.10 | 6.25 | 6.23 |
| 370 | 7.70 | 7.55 | 7.40 | 7.35 | 7.50 |
| 950 | 8.20 | 8.30 | 8.10 | 8.15 | 8.19 |
| 1900 | 9.70 | 9.20 | 9.70 | 9.50 | 9.53 |
| Control | 0 | 0 | 0 | 0 | 0 |

EXPERIMENT 4

The present substance was dissolved in Tris buffer solution in an icecooled test tube to produce solutions of protein concentration, 1125, 225, and 150 μg/ml respectively. 0.3 ml of each solution was mixed with 0.05 ml of a solution of purified human plasminogen, 15 CTA unit/ml and 0.1 ml of a solution of thrombin-Ca (50 unit—0.1 M/ml). To the resulting mixed solution was added 0.05 ml of a solution of purified human fibrinogen, 2.6% and the resulting solution was placed in a warm bath of 37° C. to form fibrin clot, and the time adding said fibrinogen solution till the fibrin clot dissolved was measured. The results are shown in Table 3.

At the same time, in place of this solution, a control using physiological saline was left alone for more than 6 hours but the fibrin clot could not be dissolved.

TABLE 3

| Protein concentration of present substance (μg/ml) | Time of dissolving fibrin clot (minutes) |
|---|---|
| 1125 | 70 |
| 225 | 143 |
| 150 | 307 |

EXPERIMENT 5

The substance was dissolved in Tris-HCl buffer solution to produce a solution of protein concentration, 370 μg/ml and was caused to act on a standard fibrin plate. After 20 hours, the diameter of the dissolved ring was measured. The results are shown in Table 4.

TABLE 4

| Poured amount of substance (μl) | Diameter of dissolved ring (mm) |
|---|---|
| 5 | 7.65 |
| 10 | 8.49 |
| 20 | 9.32 |

EXPERIMENT 6

1 ml of human flesh blood with the addition of citric acid and 0.1 ml of 0.25 M CaCl$_2$ solution were put in a plastic tube, internal diameter 3 mm and length 270 mm. Both ends of the tube were joined together to form a loop which was then rotated for 30 minutes at 37° C. to complete the formation of thrombus. The substance of this invention was dissolved in fresh human blood to produce solutions of protein concentration 0.24 mg/ml and 1.4 mg/ml respectively. These solutions were added to said thrombus and the loop thus treated was rotated for 4 hours at 37° C. after which the remaining thrombus was withdrawn from the tube and homogenized with distilled water so as to be dissolved. The amount of hemoglobin was measured at wavelength 540 nm by colorimetry to determine the fibrinolytic action of the substance. The results are shown in Table 5.

TABLE 5

| Protein concentration of substance (mg/ml) | Percentage of dissolving thrombus (%) |
|---|---|
| 0.24 | 11 |
| 1.4 | 60 |

BRIEF DESCRIPTION OF DRAWINGS

In FIG. 4, there are shown the respective peaks of amino acids as follows.

Figure 1:
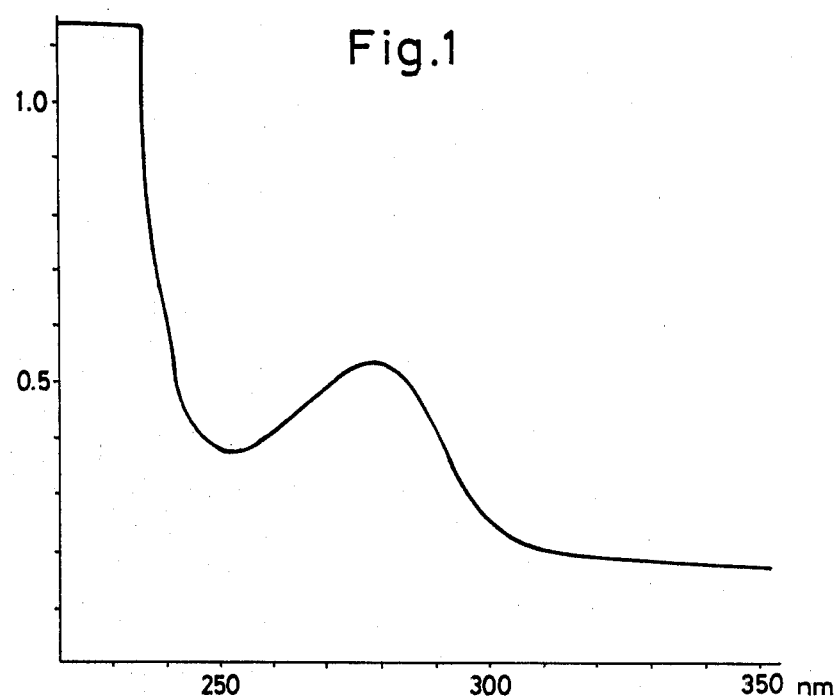
FIG. 1 shows an ultraviolet absorption spectrum of the substance.
Figure 2:
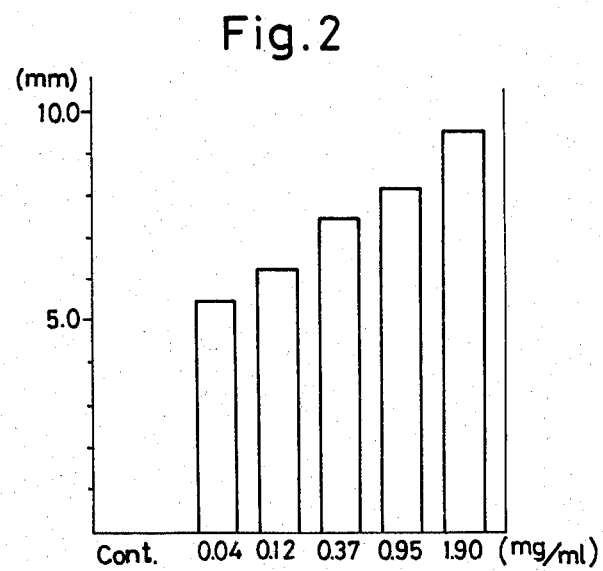
FIG. 2 shows a graph of the action of the substance on plasminogen.
Figure 3:
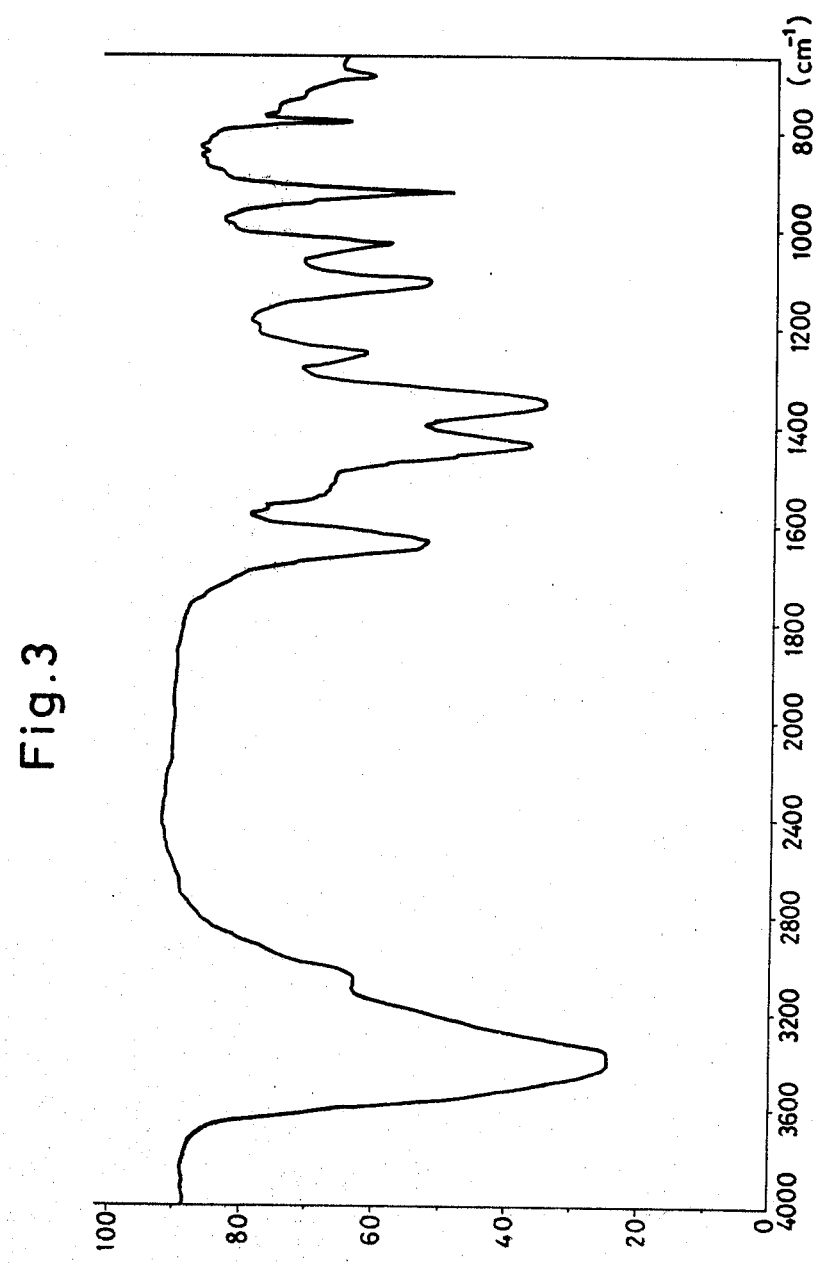
FIG. 3 shows an infrared absorption spectrum of the substance.
Figure 4:
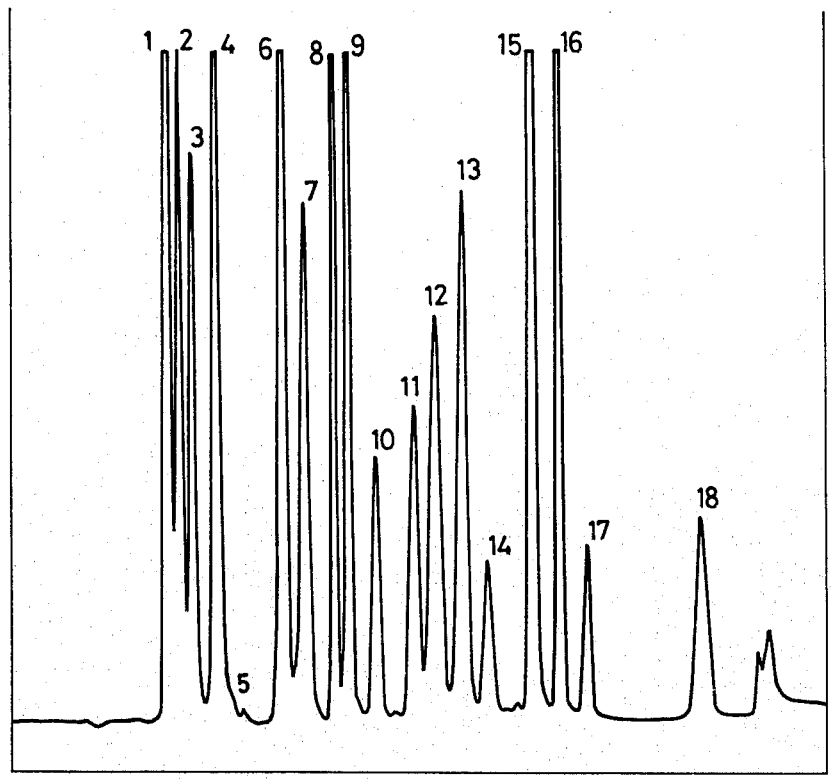
FIG. 4 shows a chart of amino acid composition of the substance by an aminoacid analyser.

| 1 | Aspartic acid | 2 | Threonine |
|---|---|---|---|
| 3 | Serine | 4 | Glutamic acid |
| 5 | Proline | 6 | Glycine |
| 7 | Alanine | 8 | Cystine |
| 9 | Valine | 10 | Methionine |
| 11 | Isoleucine | 12 | Leucine |
| 13 | Tyrosine | 14 | Phenylalanine |
| 15 | Lysine | 16 | Ammonia |
| 17 | Histidine | 18 | Arginine |

BEST MODE FOR CARRYING OUT THE INVENTION

For the purpose of clarifying the present invention further, a preferred embodiment for manufacture of the present substance will be described hereinbelow.

(EXAMPLE)

3 g of freezedried crude venom of *Trimeresurus flavoviridis* Hallowell is dissolved in 15 ml of 0.02 M boric acid buffer solution (pH 7.5) at ordinary temperature. The resulting solution is poured into a column, 5×90 cm filled with Sephadex (G-75) and the resulting solution is eluted in 0.02 M boric acid buffer solution (pH 7.5) at an eluting speed, 60 ml/hr at 5° C. and a fraction having fibrinolytic activity is collected and subjected to dialysis in distilled water. Then the dialysed internal solution of dialysis is freezedried. 100 mg of this freezedried material is dissolved in 40 ml of 0.05 M sodium acetate buffer solution (pH 6.0) and the resulting solution is adsorbed in a column, 1.5×40 cm filled with CM cellulose and eluted by slowly increasing salt concentration in said sodium acetate buffer solution till it becomes 0.3 M and a fraction having the largest activity of fibrinolysis is collected and freezedried. Subsequently, 50 mg of this fraction is dissolved in 2 ml of 0.02 M boric acid buffer solution (pH 7.5) and the resulting solution is poured into a column, 35×90 cm filled with Sephadex (G-50) and eluted at 5° C. in 0.02 M boric acid buffer solution and then a fraction of the largest activity of fibrinolysis is collected. This fraction proves to be a uniform material by SDS electrophoresis. The percentage of the substance is 3%.

I claim:

1. A method of manufacturing a substance having the activity of a plasminogen activator, which comprises subjecting a solution of venom of Trimeresursur to multiple chromatography consisting essentially of a combination of:

providing a first molecular sieve chromatography using Sephadex G-75 or G-100 as a stationary phase; thereafter providing a second molecular sieve chromatography using Sephadex G-50 as a stationary phase; and at a time before or after or intermediate said first and second chromatographies, carrying out an ion exchange chromatography using a cation exchange body as a stationary phase; fractionating each protein-containing solution eluted in turn during each stage of said first, second and ion exchange chromatography using a buffer solution of electrolyte with pH 6-8 as a mobile phase; confirming the plasminogen activator activity of each of the fractionated portions; collecting the fractionated portions having the largest plasminogen activator activity; dializing said largest activity fractionated portions in distilled water; and subjecting said largest activity portions to an operation of separation by subsequent chromatography, thereby singly isolating a substance with plasminogen activator activity.

2. A manufacturing method, as claimed in claim 1, which comprises using carboxylmethyl cellulose as said cation exchange body.

3. A manufacturing method, as claimed in claim 1, which comprises using one of a process for measuring an area of fibrinolysis of a fibrin plate or a Chandler Loop Test in confirming the activity of plasmin activator.

4. A manufacturing method, as claimed in claim 1, wherein said buffer solution of electrolyte with pH 6-8 is a solution selected from the group consisting of sodium citrate buffer solution, acetic acid buffer solution, phosphoric acid buffer solutions and boric acid buffer solutions.

5. A method of manufacturing a substance with the activity of a plasminogen activator, which comprises:

subjecting the venom of *Trimeresursur flavoviridis* to column chromatography using one of Sephadex G75 and G-100 as a stationary phase; confirming the activity of a plasminogen activator in each fractionated portion obtained by the venom thus treated being eluted in boric acid buffer solution, collecting its portion having the strongest activity of a plasminogen activator and, after dialyzing these collected portions in distilled water, freeze-drying said collected portions; subsequently subjecting said collected and freezedried portions to column chromatography using carboxymethyl cellulose as a stationary phase so as to be eluted by the use of a sodium acetate buffer solution; collecting the fractions of the last-mentioned chromatography having the strongest activity of a plasminogen activator; freeze-drying the last-mentioned fractions and further subjecting said last-mentioned fractions thus freeze-dried, to column chromatography using Sephadex G-50 as a stationary phase so as to be eluted in boric acid buffer solution; and collecting fractions of the Sephadex G-50 chromatography having the strongest activity of a plasminogen activator.

6. A manufacturing method, as claimed in claim 5, which comprises using one of a process for measuring the dissolved area of a standard fibrin plate or a Chandler Loop Test for confirming the activity of a plasminogen activator.

7. A substance with a strong plasminogen activator activity obtained by subjecting a solution of venom of Trimeresursur to multiple chromatography consisting essentially of a combination of: providing a first molecular sieve chromatography using Sephadex G-75 or G-100; thereafter providing a second molecular sieve chromatography using Sephadex G-50 as a stationary phase; and, at a time before or after or intermediate said first and second chromatographies, carrying out ion exchange chromatography using a cation exchange body as a stationary phase; fractionating each protein-containing solution eluted in turn during each stage of said first second and ion exchange chromatographies using a buffer solution of electrolyte with pH 6-8 as a mobile phase; confirming the plasminogen activator activity of each of the fractionated portions; collecting the fractionated portions having the largest plasminogen activator activity dialyzing said largest activity fractionated portions in distilled water; and subjecting said largest activity portions to an operation of separation by subsequent chromatography, thereby singly isolating a substance with plasminogen activator activity, which substance has its maximal absorption spectrum in the proximity of ultraviolet ray, 278 nm and infrared ray, around 3400 cm$^{-1}$ (large scale), 1640 cm$^{-1}$ (medium scale), 14355 cm$^{-1}$ (large), 1350 cm$^{-1}$ (large), 1250$^{-1}$ (small scale), 1100 cm$^{-1}$ (medium), 1025 cm$^{-1}$ (small), 925 cm$^{-1}$ (medium) and 780 cm$^{-1}$ (small) respectively and having a molecular weight within the range of 28,000–35,000 and observed to have a glycoprotein having a total mount of nitrogen, 12.4±1%, being soluble in water and capable of operating a plasminogen activator, the amino acids of the substance being present in a relative N mol quantity as follows,

| Aspartic acid | 15.366 |
| --- | --- |
| Threonine | 7.132 |
| Serine | 5.578 |
| Glutamic acid | 9.797 |
| Glycine | 9.475 |
| Alanine | 7.668 |
| Cystine | 5.454 |
| Valine | 7.422 |
| Methionine | 2.936 |
| Isoleucine | 4.836 |
| Leucine | 7.215 |
| Tyrosine | 8.923 |
| Phenylalanine | 2.895 |
| Lysine | 17.729 |
| Ammonia | 13.278 |
| Histidine | 1.793 |
| Arginine | 3.674. |

* * * * *